(12) United States Patent
Hasenberg et al.

(10) Patent No.: US 10,426,547 B2
(45) Date of Patent: Oct. 1, 2019

(54) SURGICAL LASER SYSTEM AND LASER FIBER

(71) Applicant: Boston Scientific Scimed, Inc., Maple Grove, MN (US)

(72) Inventors: Thomas Charles Hasenberg, Campbell, CA (US); Rongwei Jason Xuan, Fremont, CA (US); Brian P. Watschke, Minneapolis, MN (US); Douglas Lawrence Evans, Andover, MN (US); Guangjian Wang, Falcon Heights, MN (US); Steven Yihlih Peng, Fremont, CA (US); Wen-Jui Ray Chia, Sunnyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 15/954,888

(22) Filed: Apr. 17, 2018

(65) Prior Publication Data

US 2018/0235699 A1    Aug. 23, 2018

Related U.S. Application Data

(63) Continuation of application No. 14/434,038, filed as application No. PCT/US2013/065181 on Oct. 16, 2013, now Pat. No. 9,968,403.
(Continued)

(51) Int. Cl.
*A61B 18/22*    (2006.01)
*A61B 18/26*    (2006.01)
(Continued)

(52) U.S. Cl.
CPC ............. *A61B 18/22* (2013.01); *A61B 18/26* (2013.01); *A61B 2018/00511* (2013.01);
(Continued)

(58) Field of Classification Search
CPC .......... A61B 18/26; A61B 2018/00511; A61B 18/22
(Continued)

(56) References Cited

U.S. PATENT DOCUMENTS

| 2003/0082105 A1 | 5/2003 | Fischman et al. |
| 2006/0241572 A1 | 10/2006 | Zhou |

(Continued)

FOREIGN PATENT DOCUMENTS

| WO | 2011034938 A2 | 3/2011 |
| WO | 2011034938 A3 | 3/2011 |
| WO | 2014062767 A1 | 4/2014 |

OTHER PUBLICATIONS

International Search Report and Written Opinion of PCT/US2013/065181, dated Dec. 10, 2013.
(Continued)

*Primary Examiner* — Daniel L Cerioni
(74) *Attorney, Agent, or Firm* — Bookoff McAndrews, PLLC

(57) ABSTRACT

An optical device including an optical fiber having a longitudinal axis and an optical fiber core with a distal end having a distal terminating end configured to discharge a first laser energy in a first direction and a second laser energy in a second direction. The optical device also includes a fiber cap having an interior cavity and an opening to the interior cavity, where the distal end of the optical fiber core is received within the interior cavity through the opening. A cladding is included on the distal end of the optical fiber core between the optical fiber core and the fiber cap.

20 Claims, 3 Drawing Sheets

Related U.S. Application Data

(60) Provisional application No. 61/714,453, filed on Oct. 16, 2012.

(51) Int. Cl.
*A61B 18/00* (2006.01)
*A61B 18/20* (2006.01)

(52) U.S. Cl.
CPC ............... *A61B 2018/00517* (2013.01); *A61B 2018/00577* (2013.01); *A61B 2018/00589* (2013.01); *A61B 2018/00601* (2013.01); *A61B 2018/00625* (2013.01); *A61B 2018/00898* (2013.01); *A61B 2018/207* (2013.01); *A61B 2018/2266* (2013.01); *A61B 2018/2272* (2013.01)

(58) Field of Classification Search
USPC ......................................................... 606/15
See application file for complete search history.

(56) References Cited

U.S. PATENT DOCUMENTS

| | | |
|---|---|---|
| 2007/0147752 A1 | 6/2007 | Weisberg et al. |
| 2007/0219601 A1 | 9/2007 | Neuberger |
| 2008/0108867 A1 | 5/2008 | Zhou |
| 2009/0035448 A1* | 2/2009 | Flanagan ................ A61L 27/16 427/2.24 |
| 2009/0105698 A1 | 4/2009 | Hodel et al. |
| 2009/0287198 A1 | 11/2009 | Hanley et al. |
| 2009/0326525 A1 | 12/2009 | Hixon et al. |
| 2010/0016845 A1 | 1/2010 | Hanley et al. |
| 2010/0262131 A1* | 10/2010 | Neuberger ............. A61B 18/22 606/16 |
| 2011/0118715 A1 | 5/2011 | Zerfas |
| 2011/0196356 A1 | 8/2011 | Neuberger |
| 2012/0029604 A1 | 2/2012 | Sun et al. |
| 2012/0152453 A1 | 6/2012 | Chia et al. |
| 2012/0157982 A1 | 6/2012 | Anderson et al. |
| 2013/0123769 A1* | 5/2013 | Khatchaturov ........ A61B 18/22 606/16 |
| 2014/0188096 A1 | 7/2014 | Chia et al. |

OTHER PUBLICATIONS

EPO Communication for European Patent Application No. 13 78 3204.4, dated Jun. 11, 2015.

* cited by examiner

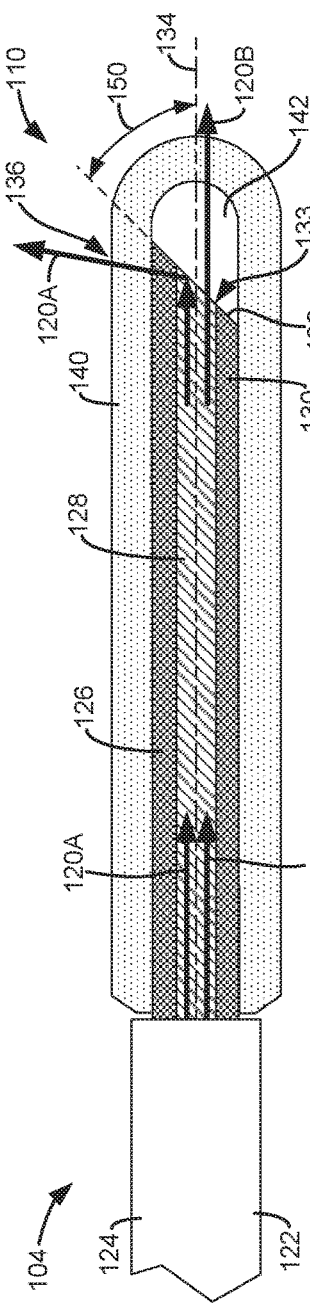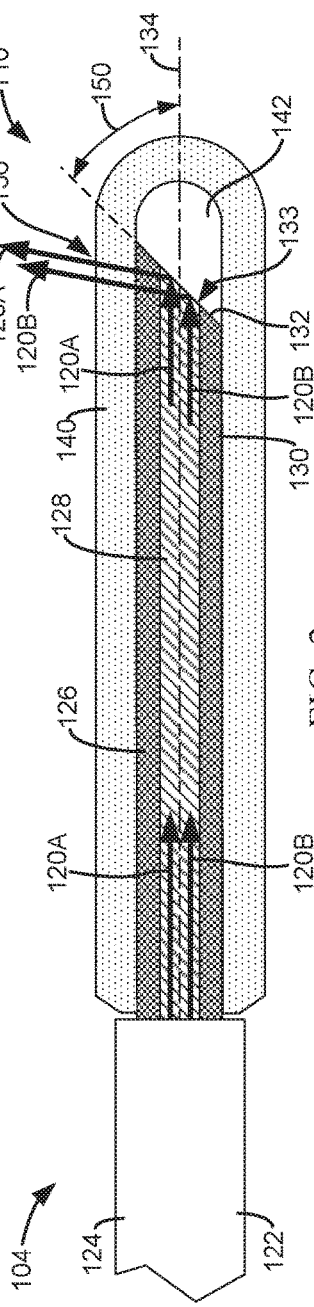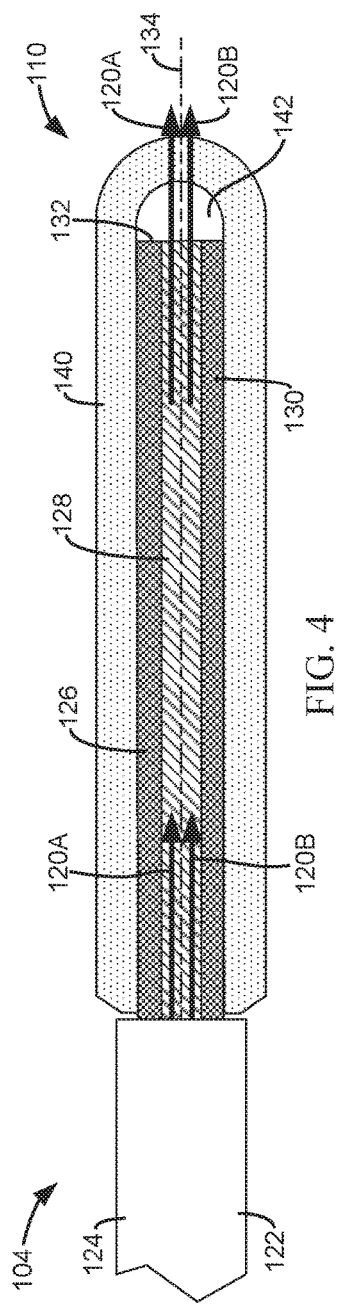

SURGICAL LASER SYSTEM AND LASER FIBER

CROSS-REFERENCE TO RELATED APPLICATION(S)

This patent application is a continuation of U.S. Nonprovisional application Ser. No. 14/434,038, filed Apr. 7, 2015, which is a § 371 National Stage Application of International Application No. PCT/US2013/065181, filed Oct. 16, 2013, which claims the benefit of U.S. Provisional Application Ser. No. 61/714,453, filed Oct. 16, 2012 under 35 U.S.C. § 119(e), the entireties of each of which are incorporated herein by reference.

BACKGROUND

Embodiments of the present invention generally relate to surgical laser systems and, more specifically, to a split laser fiber and a surgical tool that includes the split laser fiber.

Medical lasers have been used in various practice areas, such as, for example, urology, neurology, otorhinolaryngology, general anesthetic ophthalmology, dentistry, gastroenterology, cardiology, gynecology, and thoracic and orthopedic procedures. Generally, these procedures require precisely controlled delivery of laser energy as part of the treatment protocol. Surgical laser systems typically generate the laser energy in a laser resonator. The laser energy is delivered to a targeted treatment site through a laser fiber.

Different laser surgical treatments often require different types of optical fibers. For instance, a side-firing optical fiber delivers or discharges the laser energy in a lateral direction relative to the longitudinal axis of the fiber. This type of fiber is typically used in cavity wall ablation treatments, such as those used to treat benign prostatic hyperplasia (BPH), for example. An end-firing optical fiber discharges the laser energy along the longitudinal axis of the fiber. Exemplary uses of the end-firing optical fiber include ablating tumors and disintegrating kidney or bladder stones.

Additionally, different laser surgical treatments may require the delivery of different wavelengths of laser energy. For instance, the laser energy used to ablate tissue in a BPH laser treatment may be different from that selected to cut tissue, or disintegrate kidney or bladder stones.

SUMMARY OF THE INVENTION

In one embodiment, the present invention is directed to an optical device having an optical fiber with a longitudinal axis and an optical fiber core. The optical fiber core includes a distal end with a distal terminating end configured to discharge a first laser energy in a first direction and a second laser energy in a second direction. The optical device also includes a fiber cap having an interior cavity and an opening to the interior cavity, where the distal end of the optical fiber core is received within the interior cavity through the opening. In addition, a cladding is included on the distal end of the optical fiber core between the optical fiber core and the fiber cap.

In another embodiment, the present invention is directed to a surgical laser system including a first laser source and a second laser source. The surgical laser system also includes a laser fiber optically coupled to the first and second laser sources with a probe tip configured to (1) discharge laser energy from the first laser source in a first direction and (2) discharge laser energy from the second laser source in a second direction.

In a further embodiment, the present invention is directed to an optical device including an optical fiber having a longitudinal axis and an optical fiber core. The optical fiber core includes a distal end with a distal terminating end having a polished beveled surface with a coating thereon. The coating promotes reflection of a first laser energy having a first wavelength and transmission of a second laser energy having a second wavelength. The optical device also includes a fiber cap having an interior cavity and an opening to the interior cavity, where the distal end of the optical fiber core is received within the interior cavity through the opening.

BRIEF DESCRIPTION OF THE DRAWINGS

FIG. 2 is a cross-sectional view of a probe tip according to an embodiment of the invention.

FIG. 3 is a cross-sectional view of a probe tip according to an embodiment of the invention.

FIG. 4 is a cross-sectional view of a probe tip according to an embodiment of the invention.

DETAILED DESCRIPTION OF ILLUSTRATIVE EMBODIMENTS

Figure 1:
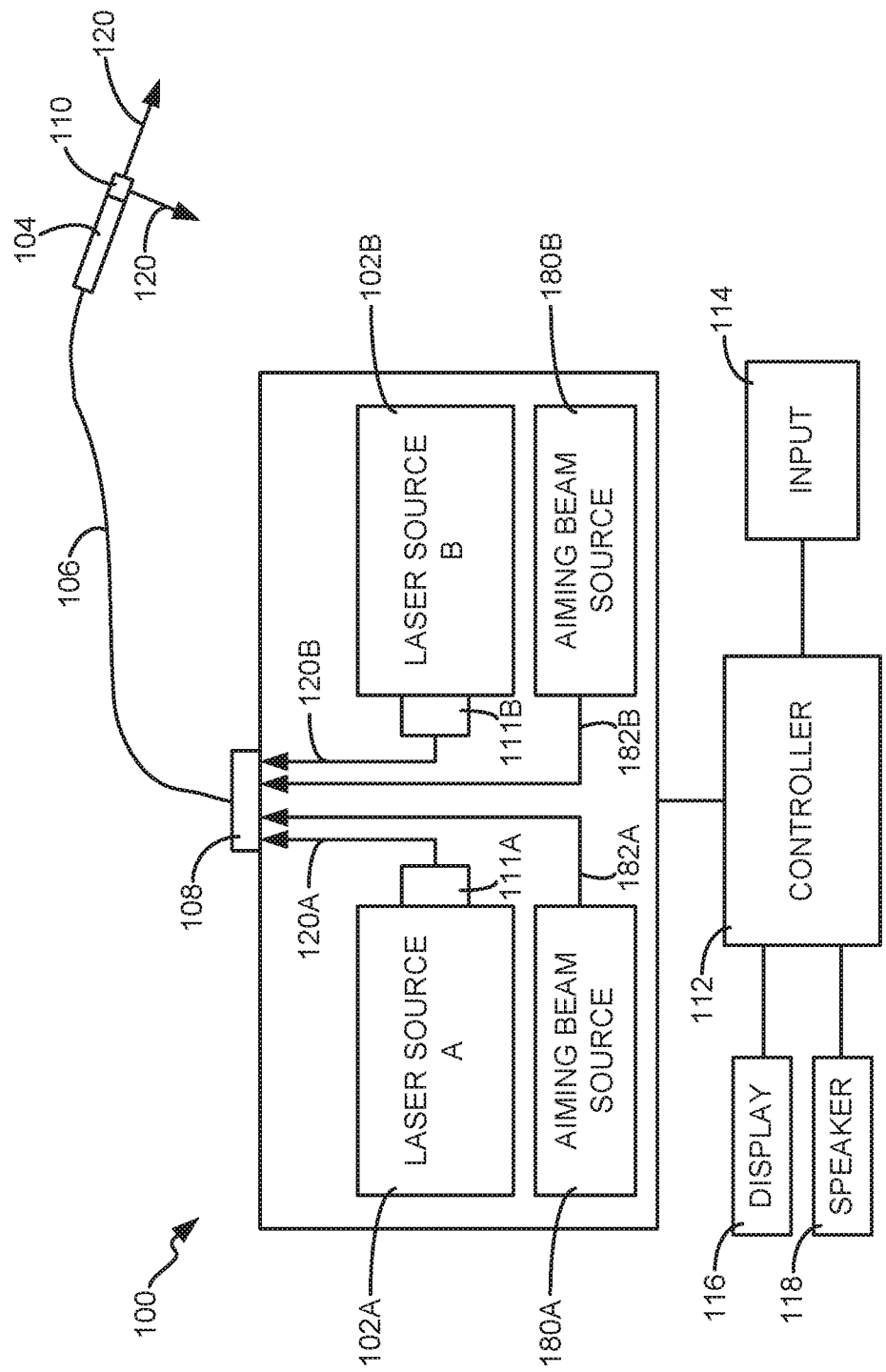
FIG. 1 is a schematic diagram of an exemplary surgical laser system in accordance with embodiments of the invention.

Embodiments of the invention are described more fully hereinafter with reference to the accompanying drawings. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art. Elements that are identified using the same or similar reference characters refer to the same or similar elements.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

It will be understood that, although the terms first, second, etc. may be used herein to describe various elements, these elements should not be limited by these terms. These terms are only used to distinguish one element from another. Thus, a first element could be termed a second element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As will further be appreciated by one of skill in the art, the present invention may be embodied as methods, systems, and/or computer program products. Accordingly, the present invention may take the form of an entirely hardware embodiment, an entirely software embodiment or an embodiment combining software and hardware aspects. Furthermore, the present invention may take the form of a computer program product on a computer-usable storage medium having computer-usable program code embodied in the medium. Any suitable computer readable medium may be utilized including hard disks, CD-ROMs, optical storage devices, or magnetic storage devices.

The computer-usable or computer-readable medium referred to herein as "memory" may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

The invention is also described using flowchart illustrations and block diagrams. It will be understood that each block (of the flowcharts and block diagrams), and combinations of blocks, can be implemented by computer program instructions. These program instructions may be provided to a processor circuit, such as a microprocessor, microcontroller or other processor, such that the instructions which execute on the processor(s) create means for implementing the functions specified in the block or blocks. The computer program instructions may be executed by the processor(s) to cause a series of operational steps to be performed by the processor(s) to produce a computer implemented process such that the instructions which execute on the processor(s) provide steps for implementing the functions specified in the block or blocks.

Accordingly, the blocks support combinations of means for performing the specified functions, combinations of steps for performing the specified functions and program instruction means for performing the specified functions. It will also be understood that each block, and combinations of blocks, can be implemented by special purpose hardware-based systems which perform the specified functions or steps, or combinations of special purpose hardware and computer instructions.

FIG. 1 is a schematic diagram of an exemplary surgical laser system 100 in accordance with embodiments of the present invention. In one embodiment, the system 100 includes at least one laser source, generally referred to as 102, and a laser fiber 104. Each of the laser sources 102 generates electromagnetic radiation or laser energy in the form of a laser beam in accordance with conventional techniques. The laser fiber 104 includes a waveguide 106 that is coupled to the laser energy generated by the laser source 102 through a suitable optical coupling 108. The laser fiber 104 includes a probe tip 110 where the laser energy is discharged to a desired laser treatment site. Embodiments of the probe tip 110 are configured to discharge the laser energy laterally relative to a longitudinal axis of the laser fiber 104 and/or substantially along the longitudinal axis of laser fiber 104. The laser fiber 104 may be supported by an endoscope or cystoscope during laser treatments in accordance with conventional techniques.

Control of the discharge of the laser energy through the optical fiber 104 may be provided through a shutter mechanism, generally referred to as 111, that is triggered by a suitable input from the physician, such as a foot pedal. Other conventional techniques may also be used to control the discharge of the laser energy through the laser fiber 104.

In one embodiment, the system 100 includes a controller 112 that includes one or more processors that are configured to execute program instructions stored in memory of the system 100 and perform various functions in accordance with embodiments described herein in response to the execution of the program instructions. These functions include, for example, the control of the laser sources 102 and the generation and delivery of laser energy through the laser fiber 104, and other functions.

In one embodiment, the controller 112 receives input commands from one or more input devices 114, such as a keyboard, a foot pedal, touch screen, or other conventional input device of surgical laser systems. The controller 112 is configured to perform various functions responsive to the commands received from the one or more input devices 114 in accordance with conventional surgical laser systems.

In one embodiment, the system 100 includes a display 116. Information regarding the system 100, such as settings for the system, and other information may be provided on the display 116 under the control of the controller 112, in accordance with conventional techniques.

In one embodiment, the system 100 includes a speaker 118. In one embodiment, the speaker 118 can provide an audio output indicating a warning, a notification, or other information.

In accordance with one embodiment, the surgical laser system 100 includes at least two laser sources 102, such as laser source 102A and 102B shown in FIG. 1. Laser source 102A is configured to generate laser energy 120A while laser source 102B is configured to generate laser energy 120B. Shutter mechanisms 111A and 111B respectively control the discharge of the laser energy 120A and 120B. Alternatively, a single shutter mechanism may be utilized if the laser energy 120A and 120B is intended to be discharged simultaneously.

In one embodiment, the laser energy 120A is different than the laser energy 120B. In one embodiment, the laser energy 120A is at a different power than the laser energy 120B. In accordance with another embodiment, the laser energy 120A has a different wavelength than the laser energy 120B.

The different types of laser energy 120 generated by the laser sources 102 of the surgical laser system 100 can be used to perform different laser treatments. For instance, green or blue laser energy having a wavelength in the range of 300-600 nanometers, which is useful in performing tissue ablation treatments, such as those used to treat BPH, may be generated by the laser source 102A, while the laser source 102B may generate laser energy having a wavelength of around 2000 nanometers, which is useful in laser lithotripsy to disintegrate kidney or bladder stones, for example. Alternatively, the laser sources 102A and 102B may produce laser energy 120 having a similar wavelength but at different power levels.

FIGS. 2-4 are cross-sectional views of probe tips 110 of laser fibers 104 in accordance with embodiments of the present invention. As mentioned above, some laser treatments utilize a side-firing laser fiber 104 or probe tip 110 to perform one type of laser treatment, and an end-firing laser fiber 104 or probe tip 110 for performing other types of laser treatments.

Embodiments of the laser fiber 104 generally comprise an optical fiber 122 having a nylon jacket 124, cladding 126 and an optical fiber core 128, as shown in FIG. 2. However, it is understood that other forms of optical fibers or waveguides may be used for the laser fiber 104. The core 128 operates as a waveguide through which electromagnetic energy, such as the laser energy 120 travels.

In one embodiment, the probe tip 110 is formed by removing the nylon jacket 124 along with any buffer from the distal end 130 of the optical fiber 122 to expose the cladding 126. In one embodiment, a polished optical surface 132 is formed at the distal terminating end of the optical fiber core 128. In one embodiment, the polished optical surface 132 is non-perpendicular to the longitudinal axis 134 of the laser fiber 104 (i.e., beveled), as shown in FIGS. 2 and 3. In one embodiment, because of the angle 150 of the beveled surface 132 with the longitudinal axis 134, the beveled surface 132 operates to reflect substantially all of the laser energy 120 from laser energies 120A and 120B transmitted through the optical fiber core 128, laterally through a transmitting surface 136, as illustrated in FIG. 3 (side-firing). In one embodiment, the beveled surface 132 includes an anti-reflection coating that promotes transmission of one of the laser energies 120B through the beveled surface 132 generally parallel to the longitudinal axis 134 (end-firing) while reflecting the other laser energy 120A laterally through the transmitting surface 136 (side-firing) as illustrated in FIG. 2 In another embodiment, the polished optical surface is perpendicular to the longitudinal axis 134 thereby allowing both laser energies 120 A and 120B to be transmitted through the polished optical surface 132 generally parallel to the longitudinal axis 134 (end-firing) as illustrated in FIG. 4.

In one embodiment, the probe tip 110 includes a fiber cap 140 that is bonded to the optical fiber 122 using conventional techniques. In one embodiment, the fiber cap 140 seals an interior cavity 142 at the surface 132. In one embodiment, the interior cavity 142 can include a gas, liquid, air or vacuum that is sealed within the cavity 142 and which promotes total internal reflection of the laser energy 120 off the surface 132 in accordance with conventional side-firing laser fibers.

In accordance with one embodiment, as discussed in further detail below, both of the laser energy 120A generated by the laser source 102A and the laser energy 120B generated by the laser source 102B are transmitted through the core 128, reflected off the beveled surface 132 and delivered through the transmitting surface 136, as shown in FIG. 3.

In accordance with another embodiment, as discussed in further detail below, the probe tip 110 is configured to discharge laser energy 120 transmitted through the core 128 either laterally through the transmitting surface 136, or in the direction of the longitudinal axis 134, depending on the wavelength of the laser energy 120. Thus, the laser fiber 104 operates as a side-firing laser fiber for certain wavelengths of laser energy 120, and also operates as an end-firing laser fiber for other wavelengths of laser energy 120. Accordingly, as depicted in FIG. 2, in one embodiment, the laser energy 120A generated by the laser source 102A that is delivered through the core 128 may be reflected off the beveled surface 132 and transmitted through the transmitting surface 136, while the laser energy 120B generated by the laser source 102B is generally discharged through the surface 132 and along the axis 134 due to the different wavelengths of the laser energies 120A and 120B.

In one embodiment, as depicted in FIG. 2, the laser fiber 104 discharges laser energy 120B generally along the longitudinal axis 134 (end-firing mode) for laser energies 120B having a longer wavelength, while discharging laser energy 120A laterally relative to the longitudinal axis 134 through the transmission surface 136 (side-firing mode) for laser energies 120A having a relatively shorter wavelength. In one embodiment, the laser fiber 104 operates in the end-firing mode for laser energies 120B having a wavelength of approximately 1900-2100 nanometers. In one embodiment, the laser fiber 104 operates in the side-firing mode for laser energies 120A having a wavelength of approximately 300-600 nanometers. Those skilled in the art readily understand that the end-firing and side-firing modes of the laser fiber 104 may correspond to other wavelength ranges.

In accordance with another embodiment, the laser fiber 104 discharges laser energy 120B generally along the longitudinal axis 134 (end-firing mode) for laser energies 120B having a shorter wavelength, while discharging laser energy 120A laterally relative to the longitudinal axis 134 (side-firing mode) for laser energies 120A having a relatively longer wavelength. These relatively shorter and longer wavelengths may have ranges such as those mentioned above, or may other ranges as will be readily understood by those skilled in the art.

In one embodiment, as illustrated in FIG. 2, a coating 133 is applied to the polished beveled surface 132 to promote the reflection of the laser energy 120A off the beveled surface 132 and laterally through the transmitting surface 136 (side-firing), and the transmission of the laser energy 120B through the beveled surface 132 along the longitudinal axis 134 (end-firing). In one embodiment, the coating comprises a dichroic coating that transmits laser energy 120B having a longer wavelength and reflects shorter wavelength laser energy 120A. Exemplary dichroic coatings include thin-film dichroic coating in layers of varying number and thickness of dielectric thin-film coatings with different refractive indexes.

In accordance with another embodiment, the angle 150 of the polished beveled surface 132 to the longitudinal axis 134 is generally greater than that which would normally be selected in order to promote total internal reflection of laser energy 120 transmitted through the fiber core 128, such as in the probe tip 110 of FIG. 3. This increase in the angle 150 relative to conventional side-firing laser fibers is intended to promote total internal reflection of the laser energy 120 delivered by the fiber core 128 by the polished beveled surface 132 such that it is transmitted through the transmission surface 136. In accordance with exemplary embodiments, the angle 150 is within a range of 26-42 degrees, such as approximately 38 degrees.

While the probe tip 110 shown in FIG. 2 illustrates the complete reflection of the laser energy 120A off the surface 132 and through the transmission surface 136, and the complete transmission of the laser energy 120B through the surface 132, it is understood that some of the laser energy 120A is likely to be transmitted through the surface 132 and some of the laser energy 120B is likely to be reflected from the surface 132 and transmitted through the transmitting surface 136. However, the amount of laser energy 120A transmitted through the surface 132 is small in comparison to the amount of laser energy 120A reflected from the surface 132 and discharged through the transmitting surface 136. Likewise, the amount of laser energy 120B reflected from the surface 132 and discharged through the transmitting surface 136 is small compared to the amount of laser energy 120B delivered through the surface 132. The small amounts of the laser energy 120A and the laser energy 120B respectively discharged along the longitudinal axis 134 of the laser fiber 104 and laterally to the longitudinal axis 134, are sufficiently small as to avoid damage to non-targeted tissue of the patient.

In accordance with another embodiment, the probe tip 110 is configured to discharge the laser energy 120 transmitted through the fiber core 128 generally along the longitudinal axis 134 (end-firing), as shown in FIG. 4. In one embodiment, the surface 132 is approximately perpendicular to the longitudinal axis 134. Thus, in one embodiment, both the laser energy 120A and the laser energy 120B are discharged along the axis 134 (end-firing) as illustrated in FIG. 4.

Additional embodiments of the invention are directed to laser treatment methods using the surgical laser system 100 formed in accordance with one or more embodiments described above. In general, the one or more laser sources 102 of the system 100 allow the system 100 to perform different types of laser treatments without replacing the laser fiber 104. Additionally, the one or more laser sources 102 may be setup to discharge desired laser energy 120 to allow the physician to quickly switch between laser treatments without having to adjust the settings of a laser source.

When the laser fiber 104 is configured to discharge the laser energy 120 generated by the laser sources 102 in a single direction, such as laterally (side-firing) (FIG. 3) or along the longitudinal axis 134 (end-firing) (FIG. 4), different laser treatments may be performed by selecting the desired laser energy 120 (120 A or 120B) that is to be transmitted to the targeted treatment site. For instance, a first laser treatment may be performed by initialing discharging the laser energy 120A generated by the laser source 102A to the targeted site through the transmission surface 136 such that the laser fiber 104 operates in side-firing mode, or vice versa, end-firing mode. A second treatment can then be performed by switching off the laser source 102A and discharging the laser energy 120B using the laser source 102B to the same or different treatment site such that the laser fiber 104 operates in end-firing mode, or vice versa, side-firing mode.

Each of the laser energies 120 that can be discharged by the laser sources 102 can be set to perform a distinct laser treatment. For example, laser energy 120A may have a wavelength and/or a power level that is different from the laser energy 120B. This allows the physician to quickly switch between laser treatments that either require a side-firing laser or an end-firing laser.

One exemplary application for this feature may be in the treatment of uterine fibroids. Fibroids are a problem that face many women. In the United States alone, about 680,000 women develop uterine fibroids annually. Of all uterine fibroids, submucosal, intramural, and subsurosal, 15% are submucosal and lend themselves to therapies delivered hysterscopically. These types of fibroids could be ablated through a laser treatment to eliminate the need to extract the fibroid material through the cervix. However, fibroids can be found in two different types: one that is highly vascularized and one that is highly calcified. It is preferable to use different wavelengths and/or different energy levels of laser energy to ablate the different types of fibroids. The system 100 can be used to quickly switch between the desired laser energies to perform the ablation of both types of fibroids in a single laser treatment session.

Figure 5:
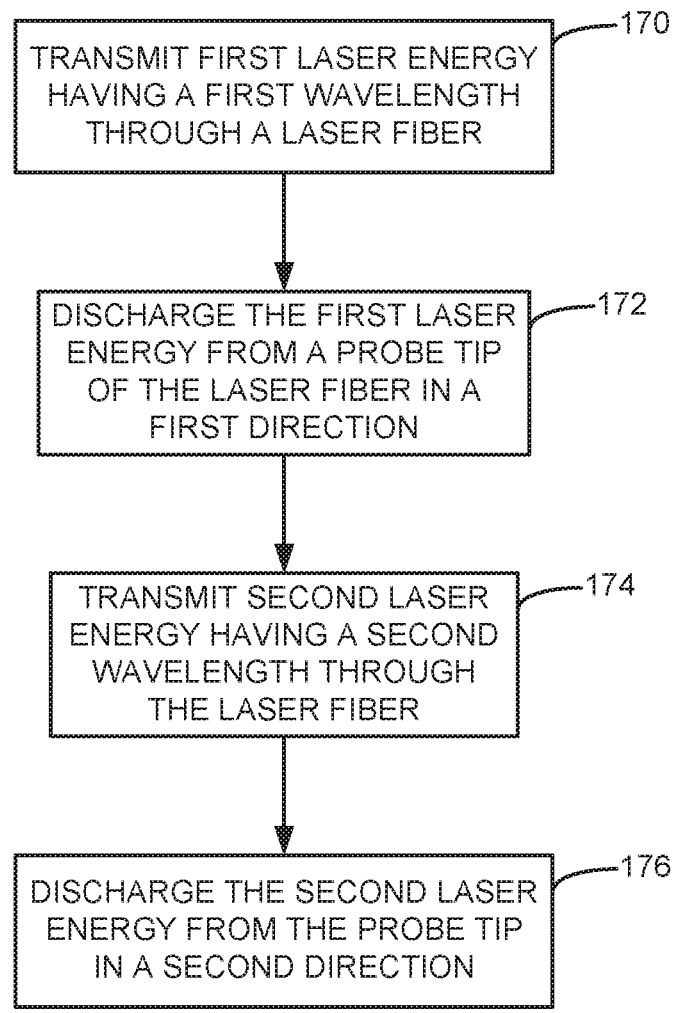
FIG. 5 is a flowchart illustrating a method of performing laser treatments in accordance with embodiments of the invention.

In some embodiments, the direction in which laser energy 120 is discharged from the probe tip 110 can be an additional variable that is used to provide multiple laser treatments using a single laser fiber 104. FIG. 5 is a flowchart illustrating embodiments of a method of performing multiple laser treatments using the laser fiber 104 of FIG. 2. At 170 of the method, laser energy 120A having a first wavelength is transmitted through the laser fiber 104, such as through the fiber core 128. At 172, the first laser energy 120A is discharged from a probe tip 110 of the laser fiber 104 in a first direction. In one embodiment, the first direction is lateral to the longitudinal axis 134 of the laser fiber 104, as illustrated in FIG. 2.

In one embodiment, steps 170 and 172 of the method correspond to a first laser treatment, such as a side-firing laser treatment. Exemplary side-firing laser treatments include ablation, coagulation, vaporization, cutting, resection or vaporesection, enucleation, or other side-fire laser treatment. In one exemplary embodiment, the treatment performed by steps 170 and 172 includes a side-firing laser treatment for BPH, in which an overgrowth of prostate cells are vaporized by the laser energy 120A discharged from the probe tip 110.

At 174 of the method, a second laser energy 120B having a second wavelength is transmitted through the laser fiber 104. Embodiments of the second wavelength include a wavelength that is different from the first wavelength, as described above. At 176, the second laser energy 120B is discharged from the probe tip 110 in a second direction that is different from the first direction. In one embodiment, the second direction is generally aligned with the longitudinal axis 134 of the laser fiber 104, as shown in FIG. 2.

In one embodiment, steps 174 and 176 correspond to a second laser treatment that is different from the first laser treatment, such as an end-firing laser treatment. Exemplary end-firing laser treatments include ablation, vaporization, coagulation, cutting, resection or vaporesection, enucleation, pulverizing or other end-fire laser treatment. In one embodiment, the end-firing laser treatment comprises a laser lithotripsy treatment to disintegrate or break up kidney or bladder stones in accordance with conventional techniques. Such stones may be encountered during a BPH laser treatment.

Thus, embodiments of the invention allow a physician to switch between laser treatments being performed on a patient without having to change out or switch the laser fiber 104, or switch or make significant adjustments to the surgical laser system 100.

Another embodiment of the invention is directed to the use of an aiming beam that provides information to the physician, which may be useful in ensuring proper setup of the surgical laser system 100 and improving safety. In one embodiment, the surgical laser system 100 includes at least one aiming beam source, generally referred to as 180, which generates an aiming laser beam, generally referred to as 182, which is optically coupled to the laser fiber 104 for discharge through the probe tip 110, as shown in FIG. 1.

Each of the aiming beams 182 corresponds to one of the laser sources 102 and is preferably discharged through the laser fiber 104 prior to triggering a discharge of the corresponding laser energy 120. In one embodiment, the aiming beam 182 provides the physician with an indication of the wavelength and/or energy level of the laser energy 120 that will be discharged. The aiming beam 182 can also indicate where the corresponding laser energy 120 will be discharged to. Thus, the aiming beam 182 may be used to target tissue or other object when the targeted site is viewed through an endoscope or other conventional tool.

In one embodiment, the aiming beam 182 is a low power laser beam that will not cause damage to the tissue of the patient. In one embodiment, the aiming beam source 180 comprises a laser diode or other suitable component.

In one embodiment, the aiming beams 182 generated by the one or more aiming beam sources 180 each have a color that identifies the wavelength and/or energy level of the laser energy 120 generated by the corresponding laser source 102. Accordingly, the discharge of the aiming beam 182 through the laser fiber 104 provides the physician with a final check that the laser energy 120 corresponding to the aiming beam 182 is of the desired wavelength and/or energy level prior to discharging the laser energy 120.

The color of the aiming beam 182 may also indicate a laser treatment that is to be performed, such as ablation, coagulation, cutting, etc. For instance, a blue or green aiming beam 182 may be discharged to indicate that the corresponding laser energy 120 is configured to perform a tissue ablation laser treatment, such as for treating BPH. Other colors of aiming beams 182 may be used to indicate other laser treatments.

The different colors of the aiming beam 182 is particularly useful when the system 100 includes multiple laser sources 102, such as laser source 102A and 102B. In one embodiment, the selection of a given laser source 102 prompts the discharge of a corresponding aiming beam 182 through the probe tip 110 prior to the discharge of the laser beam 120. For instance, when the surgical laser system 100 is set up to discharge the laser energy 120A generated by the laser source 102A, the system 100 also discharges aiming beam 182A from the aiming beam source 180A through the probe tip 110 in the same direction that the laser energy 120A will be discharged (i.e., end-firing or side-firing). Likewise, when the surgical laser system 100 is set up to discharge the laser energy 120B generated by the laser source 102B, the system 100 also discharges aiming beam 182B from the aiming beam source 180B through the probe tip 110 in the same direction that the laser energy 120B will be discharged (i.e., end-firing or side-firing).

In one embodiment, the aiming beams 182 generated by the aiming beam sources 180 are discharged from the probe tip 110 in the same direction as their corresponding laser energies 120. For instance, the system 100 may include an aiming beam source 180A that discharges an aiming beam 182A corresponding to the laser energy 120A generated by the laser source 102A. When the laser energy 120A is discharged laterally from the probe tip 110 (FIG. 2), the aiming beam 182A is also discharged laterally from the probe tip 110. In one embodiment, the aiming beam 182A has a similar wavelength as the laser energy 120A such that it is substantially reflected from the surface 132 and through the transmitting surface 136 in the same manner as the laser energy 120A. Likewise, the surgical laser system 100 may include aiming beam source 180B that is configured to produce an aiming beam 182B corresponding to the laser energy 120B generated by the laser source 102B. When the laser energy 120B is configured to be discharged along the longitudinal axis 134 of the laser fiber 104 (FIG. 2), the aiming beam 182 is also configured to be discharged along the longitudinal axis 134. Accordingly, the wavelength of the aiming beam 182B is selected such that it is transmitted through the surface 132 of the probe tip 110. As a result, when a physician selects a given laser source 102 of the surgical laser system 100, the corresponding aiming beam 182 is initially discharged through the laser fiber 104 prior to the discharge of the laser energy 120 to provide the physician with a clear understanding as to where the laser energy 120 will be discharged. As mentioned above, this allows the aiming beams 182 to be used to target tissue or other object that is to receive a dose of the laser energy 120.

Additional safety features of the surgical laser system 100 include presenting a display of the selected treatment that is to be performed by the discharge of the laser energy, an image of a probe tip illustrating the direction in which the laser energy will be discharged, information indicating the wavelength of the laser energy to be discharged, information indicating a power level of the laser energy to be discharged, and/or other information on the display 116.

In accordance with another embodiment, an audio warning is issued from the system 100 through the speaker 118. The audio warning may indicate that a laser treatment is imminent, a type of the laser treatment to be performed, a wavelength of the laser energy that is to be discharged, a power level of the laser energy that is to be discharged, a direction in which the laser energy is to be discharged from the probe tip 110, or other information.

Although the present invention has been described with reference to preferred embodiments, workers skilled in the art will recognize that changes may be made in form and detail without departing from the spirit and scope of the invention.

What is claimed is:

1. An optical device, comprising:
a controller coupled to a first treatment laser source and a first aiming laser source, wherein the controller is configured to:
in response to a request to discharge the first treatment laser source from a non-discharged state, discharge the first aiming laser source from a non-discharged state to deliver a first aiming beam in a first direction, and discharge the first treatment laser source from the non-discharged state to deliver a first laser energy in the first direction, wherein the first laser energy has a first wavelength configured to perform a first treatment, and the first aiming beam does not cause tissue damage.

2. The optical device of claim 1, wherein the controller also is coupled to a second treatment laser source and a second aiming laser source, and the controller is further configured to:
in response to a request to discharge the second treatment laser source from a non-discharged state, discharge the second aiming laser source from a non-discharged state to deliver a second aiming beam in a second direction, and discharge the second treatment laser source from the non-discharged state to deliver the second laser energy in the second direction, wherein the first direction and the second direction are different.

3. The optical device of claim 2, wherein the second laser energy has a second wavelength configured to perform a second treatment.

4. The optical device of claim 2, wherein the second aiming beam does not cause tissue damage.

5. The optical device of claim 2, further including the second treatment laser source.

6. The optical device of claim 2, further including the second aiming laser source.

7. The optical device of claim 2, further including an optical fiber having: (i) a longitudinal axis, and (ii) an optical fiber core configured to direct the first laser energy and the second laser energy along the longitudinal axis.

8. The optical device of claim 7, wherein a distal end of the optical fiber core includes a distal terminating end configured to discharge the first laser energy in the first direction, and the second laser energy in the second direction.

9. The optical device of claim 8, further including a fiber cap comprising an interior cavity and an opening to the interior cavity, wherein at least a portion of the distal end of the optical fiber core is received within the interior cavity through the opening so that the first laser energy is discharged through the fiber cap in the first direction, and the second laser energy is discharged through the fiber cap in the second direction.

10. The optical device of claim 8, wherein the distal end of the optical fiber core comprises a polished beveled surface disposed at an angle transverse to the longitudinal axis of the optical fiber.

11. The optical device of claim 10, wherein the polished beveled surface has a coating that promotes reflection of the first laser energy off of the polished beveled surface in the first direction, and transmission of the second laser energy through the polished beveled surface in the second direction.

12. The optical device of claim 11, wherein the coating is a dichroic coating that reflects the first laser energy and transmits the second laser energy.

13. The optical device of claim 7, wherein the first direction is along or parallel to the longitudinal axis, and the second direction is transverse to the longitudinal axis.

14. The optical device of claim 1, further including the first treatment laser source, and the first aiming laser source.

15. The optical device of claim 3, wherein the first treatment is configured to affect bodily tissues and the second treatment is configured to affect bladder or kidney stones.

16. The optical device of claim 1, wherein the controller is configured to provide an indication of the first direction along which the first laser energy will be discharged before the first laser energy is discharged, wherein the indication is an image of a probe tip illustrating the direction in which the first laser energy will be discharged.

17. An optical device, comprising:
a controller coupled to a first treatment laser source and a first aiming laser source, wherein the controller is configured to:
in response to a selection of the first treatment laser source while the first treatment laser source is in a non-discharged state, discharge the first aiming laser source from a non-discharged state to deliver a first aiming beam in a first direction, and discharge the first treatment laser source from the non-discharged state to deliver a first laser energy in the first direction, wherein the first laser energy has a first wavelength configured to perform a first treatment, and the first aiming beam does not cause tissue damage.

18. The optical device of claim 17, wherein the controller also is coupled to a second treatment laser source and a second aiming laser source, and the controller is further configured to:
in response to a selection of the second treatment laser source while the second treatment laser source is in a non-discharged state, discharge the second aiming laser source from a non-discharged state to deliver a second aiming beam in a second direction, and discharge the second treatment laser source from the non-discharged state to deliver the second laser energy in the second direction, wherein the first direction and the second direction are different.

19. The optical device of claim 18, wherein the second aiming beam does not cause tissue damage.

20. The optical device of claim 18, further including the second treatment laser source and the second aiming laser source.

* * * * *